(12) United States Patent
Magnuson et al.

(10) Patent No.: US 8,216,269 B2
(45) Date of Patent: Jul. 10, 2012

(54) EMBOLIC PROTECTION DEVICE HAVING REDUCED PROFILE

(75) Inventors: Mark A. Magnuson, Bloomington, IN (US); Arman H. Valaie, Bloomington, IN (US); Dharmendra Pal, Wilmington, MA (US)

(73) Assignee: Cook Medical Technologies LLC, Bloomington, IN (US)

( * ) Notice: Subject to any disclaimer, the term of this patent is extended or adjusted under 35 U.S.C. 154(b) by 740 days.

(21) Appl. No.: 11/591,880

(22) Filed: Nov. 2, 2006

(65) Prior Publication Data
US 2007/0100373 A1 May 3, 2007

Related U.S. Application Data

(60) Provisional application No. 60/732,851, filed on Nov. 2, 2005.

(51) Int. Cl.
*A61M 29/00* (2006.01)
(52) U.S. Cl. .................................................. 606/200
(58) Field of Classification Search .................. 606/200, 606/194, 114, 159, 127; 604/96.01, 509
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A | 10/1969 | Fogarty | |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |

(Continued)

FOREIGN PATENT DOCUMENTS
DE 3429850 A1 2/1986
(Continued)

OTHER PUBLICATIONS

Rubicon Embolic Filter, The Next Generation of EM, Rubicon Medical, www.rubiconmed.com.

(Continued)

*Primary Examiner* — Kathleen Sonnett
*Assistant Examiner* — Jocelin Tanner
(74) *Attorney, Agent, or Firm* — Brinks Hofer Gilson & Lione

(57) ABSTRACT

A device for capturing emboli during treatment of a stenotic lesion in a body vessel is disclosed. The device comprises a base having expanded and collapsed states, and proximal and distal portions. The distal portion has a support portion configured to deploy in the body vessel when the base is in the expanded state. The device further comprises a filter portion disposed on the distal portion of the base. The filter portion includes a lip extending to a filter body to a filter end. The filter portion is configured to engage the support portion when deployed to define an opening of the filter portion for capturing emboli. The device further comprises a collector through which the base is slideably disposed for delivery and retrieval of the device.

10 Claims, 5 Drawing Sheets

U.S. PATENT DOCUMENTS

| | | |
|---|---|---|
| 4,562,039 A | 12/1985 | Koehler |
| 4,604,094 A | 8/1986 | Shook |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A | 10/1991 | Bajaj |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |

| Patent | Kind | Date | Inventor |
|---|---|---|---|
| 6,063,113 | A | 5/2000 | Kavteladze et al. |
| 6,066,158 | A | 5/2000 | Engelson et al. |
| 6,068,645 | A | 5/2000 | Tu |
| 6,074,357 | A | 6/2000 | Kaganov et al. |
| 6,077,274 | A | 6/2000 | Ouchi et al. |
| 6,080,178 | A | 6/2000 | Meglin |
| 6,083,239 | A | 7/2000 | Addis |
| 6,086,577 | A | 7/2000 | Ken et al. |
| 6,086,605 | A | 7/2000 | Barbut et al. |
| 6,093,199 | A | 7/2000 | Brown et al. |
| 6,096,053 | A | 8/2000 | Bates |
| 6,096,070 | A | 8/2000 | Ragheb et al. |
| 6,099,549 | A | 8/2000 | Bosma et al. |
| 6,106,497 | A | 8/2000 | Wang |
| 6,126,672 | A | 10/2000 | Berryman et al. |
| 6,126,673 | A | 10/2000 | Kim et al. |
| 6,129,739 | A | 10/2000 | Khosravi |
| 6,136,016 | A | 10/2000 | Barbut et al. |
| 6,146,396 | A | 11/2000 | Konya et al. |
| 6,146,404 | A | 11/2000 | Kim et al. |
| 6,152,931 | A | 11/2000 | Nadal et al. |
| 6,152,946 | A | 11/2000 | Broome et al. |
| 6,152,947 | A | 11/2000 | Ambrisco et al. |
| 6,156,061 | A | 12/2000 | Wallace et al. |
| 6,156,062 | A | 12/2000 | McGuinness |
| 6,159,230 | A | 12/2000 | Samuels |
| 6,165,179 | A | 12/2000 | Cathcart et al. |
| 6,165,198 | A | 12/2000 | McGurk et al. |
| 6,165,199 | A | 12/2000 | Barbut |
| 6,165,200 | A | 12/2000 | Tsugita et al. |
| 6,168,579 | B1 | 1/2001 | Tsugita et al. |
| 6,168,603 | B1 | 1/2001 | Leslie et al. |
| 6,168,610 | B1 | 1/2001 | Marin et al. |
| 6,168,622 | B1 | 1/2001 | Mazzocchi |
| 6,171,327 | B1 | 1/2001 | Daniel et al. |
| 6,171,328 | B1 | 1/2001 | Addis |
| 6,174,318 | B1 | 1/2001 | Bates et al. |
| 6,179,851 | B1 | 1/2001 | Barbut et al. |
| 6,179,859 | B1 | 1/2001 | Bates et al. |
| 6,179,860 | B1 | 1/2001 | Fulton, III et al. |
| 6,179,861 | B1 | 1/2001 | Khosravi et al. |
| 6,187,025 | B1 | 2/2001 | Machek |
| 6,193,739 | B1 | 2/2001 | Chevillon et al. |
| 6,203,561 | B1 | 3/2001 | Ramee et al. |
| 6,206,931 | B1 | 3/2001 | Cook et al. |
| 6,214,025 | B1 | 4/2001 | Thistle et al. |
| 6,214,026 | B1 | 4/2001 | Lepak et al. |
| 6,221,091 | B1 | 4/2001 | Khosravi |
| 6,224,620 | B1 | 5/2001 | Maahs |
| 6,231,588 | B1 | 5/2001 | Zadno-Azizi |
| 6,231,589 | B1 | 5/2001 | Wessman et al. |
| 6,235,044 | B1 | 5/2001 | Root et al. |
| 6,235,045 | B1 | 5/2001 | Barbut et al. |
| 6,238,412 | B1 | 5/2001 | Dubrul et al. |
| 6,241,746 | B1 | 6/2001 | Bosma et al. |
| 6,245,012 | B1 | 6/2001 | Kleshinski |
| 6,245,087 | B1 | 6/2001 | Addis |
| 6,245,088 | B1 | 6/2001 | Lowery |
| 6,245,089 | B1 | 6/2001 | Daniel et al. |
| 6,251,092 | B1 | 6/2001 | Qin et al. |
| 6,251,122 | B1 | 6/2001 | Tsukernik |
| 6,254,550 | B1 | 7/2001 | McNamara et al. |
| 6,254,633 | B1 | 7/2001 | Pinchuk et al. |
| 6,258,026 | B1 | 7/2001 | Ravenscroft et al. |
| 6,258,115 | B1 | 7/2001 | Dubrul |
| 6,258,120 | B1 | 7/2001 | McKenzie et al. |
| 6,261,305 | B1 | 7/2001 | Marotta et al. |
| 6,264,672 | B1 | 7/2001 | Fisher |
| 6,267,776 | B1 | 7/2001 | O'Connell |
| 6,267,777 | B1 | 7/2001 | Bosma et al. |
| 6,273,900 | B1 | 8/2001 | Nott et al. |
| 6,273,901 | B1 | 8/2001 | Whitcher et al. |
| 6,277,125 | B1 | 8/2001 | Barry et al. |
| 6,277,126 | B1 | 8/2001 | Barry et al. |
| 6,277,138 | B1 | 8/2001 | Levinson et al. |
| 6,277,139 | B1 | 8/2001 | Levinson et al. |
| 6,280,451 | B1 | 8/2001 | Bates et al. |
| 6,287,321 | B1 | 9/2001 | Jang |
| 6,290,710 | B1 | 9/2001 | Cryer et al. |
| 6,299,604 | B1 | 10/2001 | Ragheb et al. |
| 6,306,163 | B1 | 10/2001 | Fitz |
| 6,309,399 | B1 | 10/2001 | Barbut et al. |
| 6,312,444 | B1 | 11/2001 | Barbut |
| 6,319,268 | B1 | 11/2001 | Ambrisco et al. |
| 6,325,815 | B1 | 12/2001 | Kusleika et al. |
| 6,325,816 | B1 | 12/2001 | Fulton, III et al. |
| 6,328,755 | B1 | 12/2001 | Marshall |
| 6,331,183 | B1 | 12/2001 | Suon |
| 6,331,184 | B1 | 12/2001 | Abrams |
| 6,334,864 | B1 | 1/2002 | Amplatz et al. |
| 6,336,934 | B1 | 1/2002 | Gilson et al. |
| 6,338,739 | B1 | 1/2002 | Datta et al. |
| 6,340,364 | B2 | 1/2002 | Kanesaka |
| 6,342,062 | B1 | 1/2002 | Suon et al. |
| 6,342,063 | B1 | 1/2002 | DeVries et al. |
| 6,344,048 | B1 | 2/2002 | Chin et al. |
| 6,344,049 | B1 | 2/2002 | Levinson et al. |
| 6,346,116 | B1 | 2/2002 | Brooks et al. |
| 6,348,063 | B1 | 2/2002 | Yassour et al. |
| 6,350,271 | B1 | 2/2002 | Kurz et al. |
| 6,355,051 | B1 | 3/2002 | Sisskind et al. |
| 6,358,228 | B1 | 3/2002 | Tubman et al. |
| 6,361,545 | B1 | 3/2002 | Macoviak et al. |
| 6,361,546 | B1 | 3/2002 | Khosravi |
| 6,361,547 | B1 | 3/2002 | Hieshima |
| 6,364,895 | B1 | 4/2002 | Greenhalgh |
| 6,364,896 | B1 | 4/2002 | Addis |
| 6,368,338 | B1 | 4/2002 | Konya et al. |
| 6,371,961 | B1 | 4/2002 | Osborne et al. |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,379,374 | B1 | 4/2002 | Hieshima et al. |
| 6,380,457 | B1 | 4/2002 | Yurek et al. |
| 6,383,146 | B1 | 5/2002 | Klint |
| 6,383,171 | B1 | 5/2002 | Gifford et al. |
| 6,383,174 | B1 | 5/2002 | Eder |
| 6,383,193 | B1 | 5/2002 | Cathcart et al. |
| 6,383,196 | B1 | 5/2002 | Leslie et al. |
| 6,383,205 | B1 | 5/2002 | Samson et al. |
| 6,383,206 | B1 | 5/2002 | Gillick et al. |
| 6,391,044 | B1 | 5/2002 | Yadav et al. |
| 6,391,045 | B1 | 5/2002 | Kim et al. |
| 6,391,052 | B2 | 5/2002 | Buirge et al. |
| 6,395,014 | B1 | 5/2002 | Macoviak et al. |
| 6,402,771 | B1 | 6/2002 | Palmer et al. |
| 6,402,772 | B1 | 6/2002 | Amplatz et al. |
| 6,409,742 | B1 | 6/2002 | Fulton, III et al. |
| 6,413,235 | B1 | 7/2002 | Parodi |
| 6,416,530 | B2 | 7/2002 | DeVries et al. |
| 6,419,686 | B1 | 7/2002 | McLeod et al. |
| 6,423,052 | B1 | 7/2002 | Escano |
| 6,423,086 | B1 | 7/2002 | Barbut et al. |
| 6,425,909 | B1 | 7/2002 | Dieck et al. |
| 6,428,557 | B1 | 8/2002 | Hilaire |
| 6,428,558 | B1 | 8/2002 | Jones et al. |
| 6,428,559 | B1 | 8/2002 | Johnson |
| 6,432,122 | B1 | 8/2002 | Gilson et al. |
| 6,436,112 | B2 | 8/2002 | Wensel et al. |
| 6,436,120 | B1 | 8/2002 | Meglin |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma et al. |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,454,775 | B1 | 9/2002 | Demarais et al. |
| 6,458,139 | B1 | 10/2002 | Palmer et al. |
| 6,458,145 | B1 | 10/2002 | Ravenscroft et al. |
| 6,461,370 | B1 | 10/2002 | Gray et al. |
| 6,468,290 | B1 | 10/2002 | Weldon et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,500 | B1 | 11/2002 | Kokish et al. |
| 6,485,501 | B1 | 11/2002 | Green |

| | | |
|---|---|---|
| 6,485,502 B2 | 11/2002 | Don Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 * | 2/2003 | Blackledge et al. .......... 606/200 |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 * | 3/2003 | Hopkins et al. |
| 6,530,940 B2 * | 3/2003 | Fisher ......................... 606/200 |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,856 B2 | 6/2004 | Seibold et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 * | 3/2005 | White et al. .................. 606/114 |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,936,059 B2 | 8/2005 | Belef |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |

| | | |
|---|---|---|
| 7,128,073 B1 | 10/2006 | van der Burg et al. |
| 7,166,120 B2 | 1/2007 | Kusleika |
| 7,174,636 B2 * | 2/2007 | Lowe .................. 29/896.62 |
| 7,189,249 B2 | 3/2007 | Hart et al. |
| 7,204,847 B1 | 4/2007 | Gambale |
| 7,220,271 B2 | 5/2007 | Clubb et al. |
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,731,722 B2 | 6/2010 | Lavelle et al. |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 * | 9/2001 | Okada ..................... 606/200 |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 * | 9/2002 | Ostrovsky et al. ............. 606/200 |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1 | 11/2002 | Eum et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |

| | | | | | |
|---|---|---|---|---|---|
| 2003/0023265 A1 | 1/2003 | Forber | 2003/0176884 A1 | 9/2003 | Berrada et al. |
| 2003/0032976 A1 | 2/2003 | Boucck | 2003/0176885 A1 | 9/2003 | Broome et al. |
| 2003/0032977 A1 | 2/2003 | Brady | 2003/0176886 A1 | 9/2003 | Wholey et al. |
| 2003/0040772 A1 | 2/2003 | Hyodoh et al. | 2003/0176887 A1 | 9/2003 | Petersen |
| 2003/0045897 A1 | 3/2003 | Huter et al. | 2003/0176888 A1 | 9/2003 | O'Connell |
| 2003/0045898 A1 | 3/2003 | Harrison et al. | 2003/0176889 A1 | 9/2003 | Boyle et al. |
| 2003/0050662 A1 | 3/2003 | Don Michael | 2003/0181942 A1 | 9/2003 | Sutton et al. |
| 2003/0055452 A1 | 3/2003 | Joergensen et al. | 2003/0181943 A1 | 9/2003 | Daniel et al. |
| 2003/0055480 A1* | 3/2003 | Fischell et al. ............... 623/1.11 | 2003/0187474 A1 | 10/2003 | Keegan et al. |
| 2003/0060843 A1 | 3/2003 | Boucher | 2003/0187475 A1 | 10/2003 | Tsugita et al. |
| 2003/0060844 A1 | 3/2003 | Borillo et al. | 2003/0187495 A1 | 10/2003 | Cully et al. |
| 2003/0065354 A1 | 4/2003 | Boyle et al. | 2003/0191492 A1 | 10/2003 | Gellman et al. |
| 2003/0065355 A1 | 4/2003 | Weber | 2003/0191493 A1 | 10/2003 | Epstein et al. |
| 2003/0065356 A1 | 4/2003 | Tsugita et al. | 2003/0195554 A1 | 10/2003 | Shen et al. |
| 2003/0069596 A1 | 4/2003 | Eskuri | 2003/0195555 A1 | 10/2003 | Khairkhahan et al. |
| 2003/0073979 A1 | 4/2003 | Naimark et al. | 2003/0195556 A1 | 10/2003 | Stack et al. |
| 2003/0074019 A1 | 4/2003 | Gray et al. | 2003/0199819 A1 | 10/2003 | Beck |
| 2003/0074054 A1 | 4/2003 | Duerig et al. | 2003/0199917 A1 | 10/2003 | Knudson et al. |
| 2003/0078614 A1 | 4/2003 | Salahieh et al. | 2003/0199918 A1 | 10/2003 | Patel et al. |
| 2003/0083608 A1 | 5/2003 | Evans et al. | 2003/0199919 A1 | 10/2003 | Palmer et al. |
| 2003/0083692 A1 | 5/2003 | Vrba et al. | 2003/0199920 A1 | 10/2003 | Boylan et al. |
| 2003/0083693 A1 | 5/2003 | Daniel et al. | 2003/0199921 A1 | 10/2003 | Palmer et al. |
| 2003/0088211 A1 | 5/2003 | Anderson et al. | 2003/0204168 A1 | 10/2003 | Bosma et al. |
| 2003/0088266 A1 | 5/2003 | Bowlin | 2003/0204202 A1 | 10/2003 | Palmer et al. |
| 2003/0093110 A1 | 5/2003 | Vale | 2003/0204203 A1 | 10/2003 | Khairkhahan et al. |
| 2003/0093112 A1 | 5/2003 | Addis | 2003/0208222 A1 | 11/2003 | Zadno-Azizi |
| 2003/0097094 A1 | 5/2003 | Ouriel et al. | 2003/0208224 A1 | 11/2003 | Broome |
| 2003/0097145 A1 | 5/2003 | Goldberg et al. | 2003/0208225 A1 | 11/2003 | Goll et al. |
| 2003/0100917 A1 | 5/2003 | Boyle et al. | 2003/0208226 A1 | 11/2003 | Bruckheimer et al. |
| 2003/0100918 A1 | 5/2003 | Duane | 2003/0208227 A1 | 11/2003 | Thomas |
| 2003/0100919 A1 | 5/2003 | Hopkins et al. | 2003/0208228 A1 | 11/2003 | Gilson et al. |
| 2003/0105472 A1 | 6/2003 | McAlister | 2003/0208229 A1 | 11/2003 | Kletschka |
| 2003/0105484 A1 | 6/2003 | Boyle et al. | 2003/0208253 A1 | 11/2003 | Beyer et al. |
| 2003/0105486 A1 | 6/2003 | Murphy et al. | 2003/0212428 A1 | 11/2003 | Richter |
| 2003/0109824 A1 | 6/2003 | Anderson et al. | 2003/0212429 A1 | 11/2003 | Keegan et al. |
| 2003/0109897 A1 | 6/2003 | Walak et al. | 2003/0212431 A1 | 11/2003 | Brady et al. |
| 2003/0109916 A1 | 6/2003 | Don Michael | 2003/0212432 A1 | 11/2003 | Khairkhahan et al. |
| 2003/0114879 A1 | 6/2003 | Euteneuer et al. | 2003/0212433 A1 | 11/2003 | Ambrisco et al. |
| 2003/0114880 A1 | 6/2003 | Hansen et al. | 2003/0212434 A1 | 11/2003 | Thielen |
| 2003/0120303 A1 | 6/2003 | Boyle et al. | 2003/0216774 A1 | 11/2003 | Larson |
| 2003/0120304 A1 | 6/2003 | Kaganov et al. | 2003/0220665 A1 | 11/2003 | Eskuri et al. |
| 2003/0125764 A1 | 7/2003 | Brady et al. | 2003/0220667 A1 | 11/2003 | Van der Burg et al. |
| 2003/0125765 A1 | 7/2003 | Blackledge et al. | 2003/0225418 A1 | 12/2003 | Esksuri et al. |
| 2003/0130680 A1 | 7/2003 | Russell | 2003/0225435 A1 | 12/2003 | Hunter et al. |
| 2003/0130681 A1 | 7/2003 | Ungs | 2003/0229374 A1 | 12/2003 | Brady et al. |
| 2003/0130682 A1 | 7/2003 | Broome et al. | 2003/0233117 A1 | 12/2003 | Adams et al. |
| 2003/0130684 A1 | 7/2003 | Brady et al. | 2004/0006364 A1 | 1/2004 | Ladd |
| 2003/0130685 A1 | 7/2003 | Daniel et al. | 2004/0006365 A1* | 1/2004 | Brady et al. ................... 606/200 |
| 2003/0130686 A1 | 7/2003 | Daniel et al. | 2004/0006370 A1 | 1/2004 | Tsugita |
| 2003/0130687 A1 | 7/2003 | Daniel et al. | 2004/0015152 A1 | 1/2004 | Day |
| 2003/0130688 A1 | 7/2003 | Daniel et al. | 2004/0039412 A1 | 2/2004 | Isshiki et al. |
| 2003/0135232 A1 | 7/2003 | Douk et al. | 2004/0049226 A1 | 3/2004 | Keegan et al. |
| 2003/0135233 A1 | 7/2003 | Bates et al. | 2004/0054394 A1 | 3/2004 | Lee |
| 2003/0139764 A1 | 7/2003 | Levinson et al. | 2004/0054395 A1 | 3/2004 | Lee et al. |
| 2003/0139765 A1 | 7/2003 | Patel et al. | 2004/0059372 A1 | 3/2004 | Tsugita |
| 2003/0144685 A1 | 7/2003 | Boyle et al. | 2004/0064067 A1 | 4/2004 | Ward |
| 2003/0144686 A1 | 7/2003 | Martinez et al. | 2004/0064179 A1 | 4/2004 | Linder et al. |
| 2003/0144687 A1 | 7/2003 | Brady et al. | 2004/0068271 A1 | 4/2004 | McAlister |
| 2003/0144688 A1 | 7/2003 | Brady et al. | 2004/0078044 A1 | 4/2004 | Kear |
| 2003/0144689 A1 | 7/2003 | Brady et al. | 2004/0082962 A1 | 4/2004 | Demarais et al. |
| 2003/0150821 A1 | 8/2003 | Bates et al. | 2004/0088038 A1 | 5/2004 | Dehnad et al. |
| 2003/0153935 A1 | 8/2003 | Mialhe | 2004/0093009 A1 | 5/2004 | Denison et al. |
| 2003/0153942 A1 | 8/2003 | Wang et al. | 2004/0093012 A1 | 5/2004 | Cully et al. |
| 2003/0153943 A1 | 8/2003 | Michael et al. | 2004/0093016 A1 | 5/2004 | Root et al. |
| 2003/0153944 A1 | 8/2003 | Phung et al. | 2004/0093059 A1 | 5/2004 | Lee et al. |
| 2003/0153945 A1 | 8/2003 | Patel et al. | 2004/0098022 A1 | 5/2004 | Barone |
| 2003/0158518 A1 | 8/2003 | Schonholz et al. | 2004/0098026 A1 | 5/2004 | Joergensen et al. |
| 2003/0158574 A1 | 8/2003 | Esch et al. | 2004/0098033 A1 | 5/2004 | Leeflang et al. |
| 2003/0158575 A1 | 8/2003 | Boylan et al. | 2004/0098112 A1 | 5/2004 | DiMatteo et al. |
| 2003/0163158 A1 | 8/2003 | White | 2004/0102719 A1 | 5/2004 | Keith et al. |
| 2003/0163159 A1 | 8/2003 | Patel et al. | 2004/0106944 A1 | 6/2004 | Daniel et al. |
| 2003/0167068 A1 | 9/2003 | Amplatz | 2004/0116831 A1 | 6/2004 | Vrba |
| 2003/0167069 A1 | 9/2003 | Gonzales et al. | 2004/0133232 A1 | 7/2004 | Rosenbluth et al. |
| 2003/0171769 A1 | 9/2003 | Barbut | 2004/0138696 A1 | 7/2004 | Drasler et al. |
| 2003/0171770 A1 | 9/2003 | Kusleika et al. | 2004/0153118 A1 | 8/2004 | Clubb et al. |
| 2003/0171771 A1 | 9/2003 | Anderson et al. | 2004/0158278 A1 | 8/2004 | Becker et al. |
| 2003/0171772 A1 | 9/2003 | Amplatz | 2004/0162576 A1 | 8/2004 | Barbut et al. |
| 2003/0171800 A1 | 9/2003 | Bicek et al. | 2004/0164030 A1 | 8/2004 | Lowe et al. |
| 2003/0171803 A1 | 9/2003 | Shimon | 2004/0167567 A1 | 8/2004 | Cano et al. |

| | | |
|---|---|---|
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1* | 2/2005 | Panetta et al. ............ 606/200 |
| 2005/0038503 A1 | 2/2005 | Greenhaigh |
| 2005/0043743 A1 | 2/2005 | Dennis |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009790 A1 | 1/2006 | Blake et al. |
| 2006/0009798 A1 | 1/2006 | Callister et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1127556 A2 | 8/2001 |
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Heeschen et al., Nature Medicine 7 (2001), No. 7, pp. 833-839.

Johnson et al., Circulation Research 94 (2004), No. 2, pp. 262-268.

International Search Report and Written Opinion for PCT/US2007/020300.

Brochure, "Shuttle Select™ System for Carotid Artery Access," (2004), pp. 1-3.

Brochure, "Slip-Cath® Angiographic Selective Catheters," (2004), pp. 1-6.

Finol, E.A. et al., "Performance Assessment of Embolic Protection Filters for Carotid Artery Stenting," *Modelling in Medicine and Biology IV*, (2005), vol. 8, pp. 133.

Grummon, David S. et al., Appl. Phys. Lett., 82, 2727 (2003), pp. 2727.

* cited by examiner

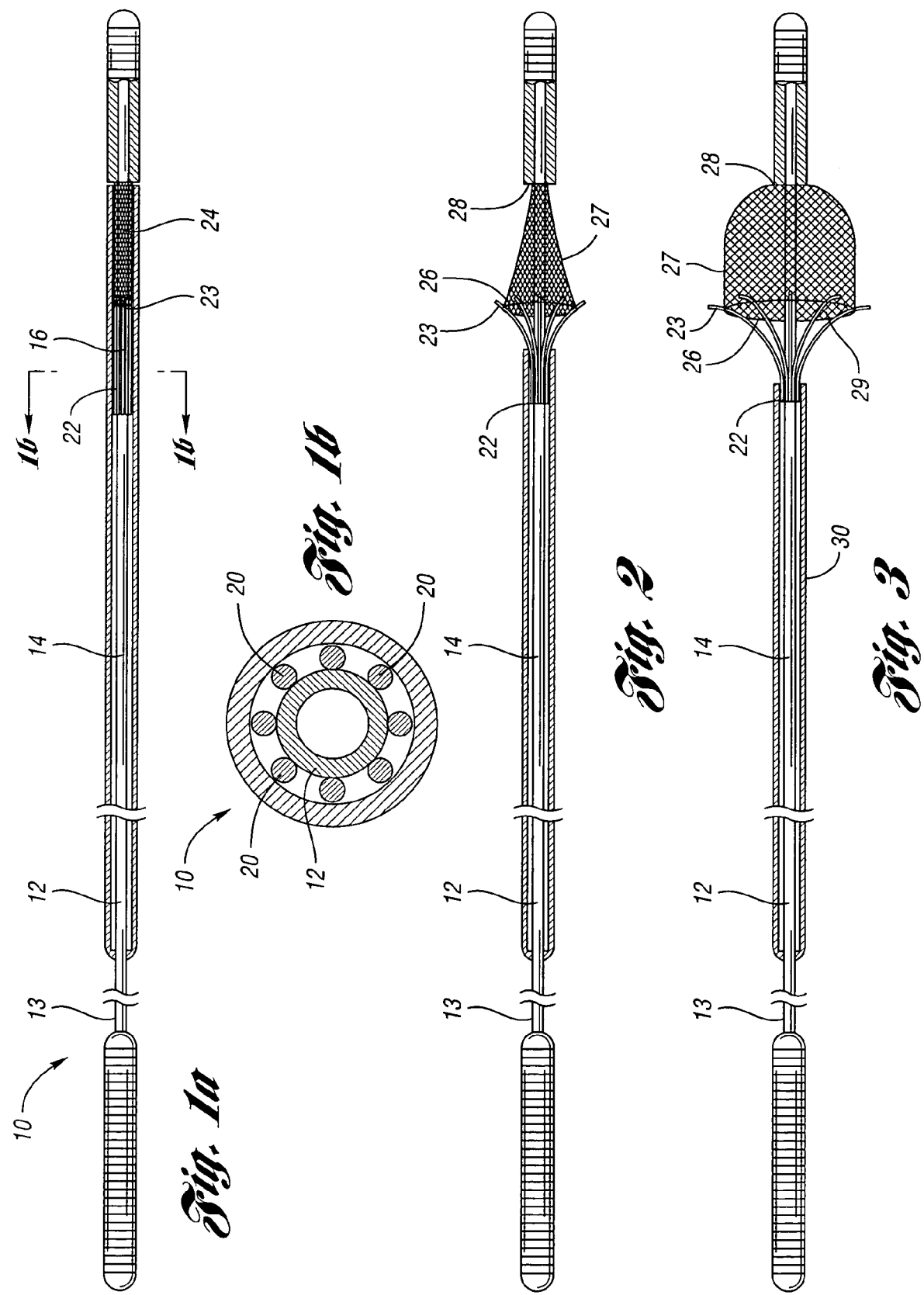

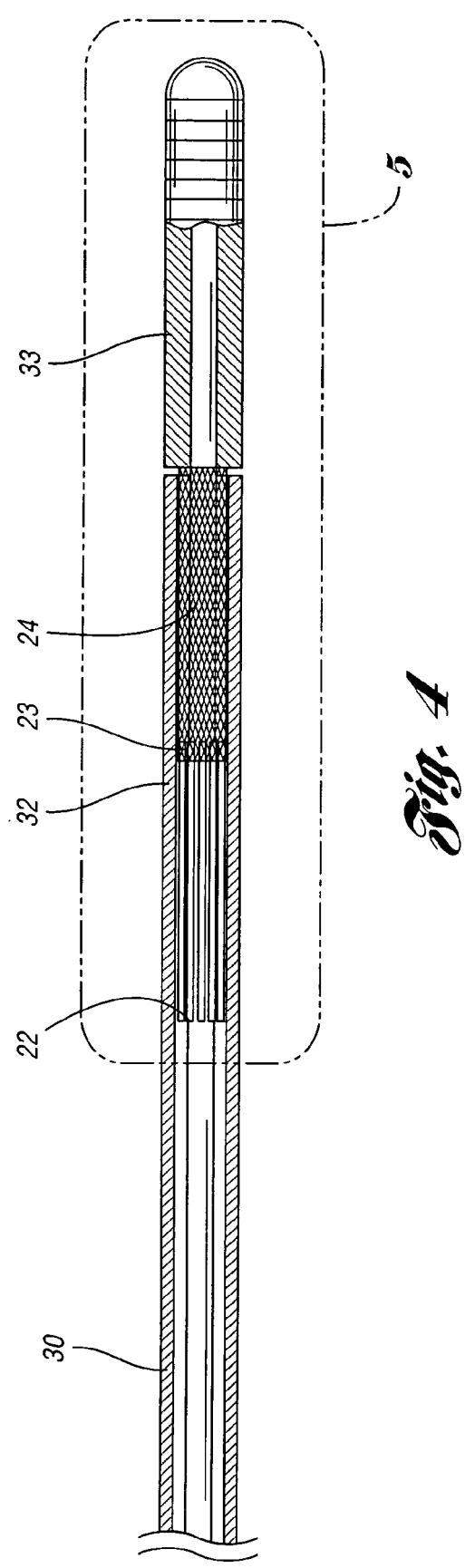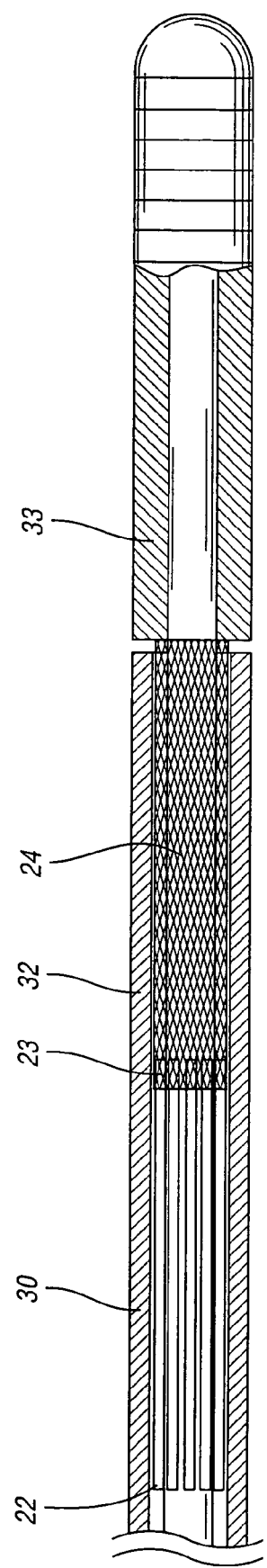

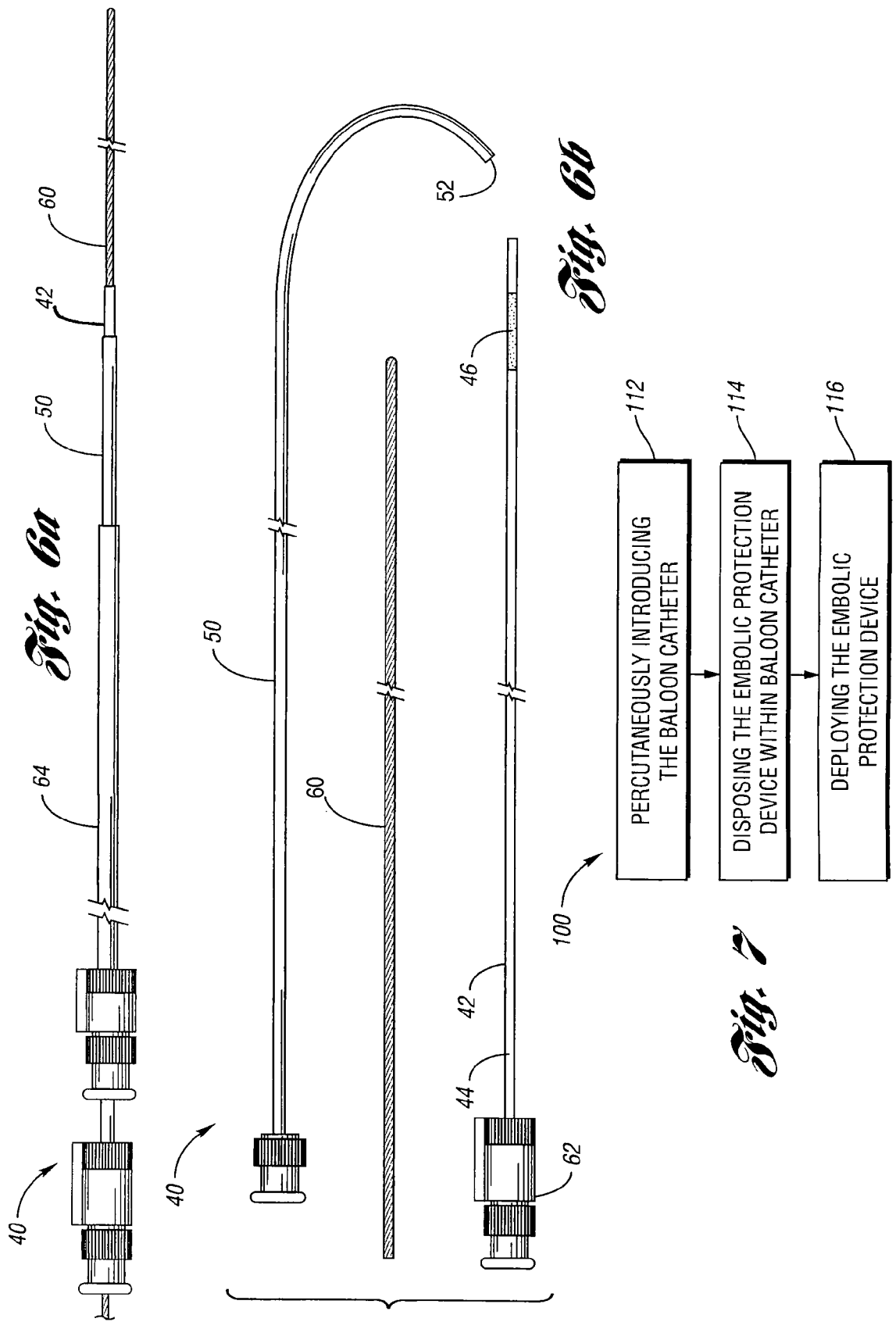

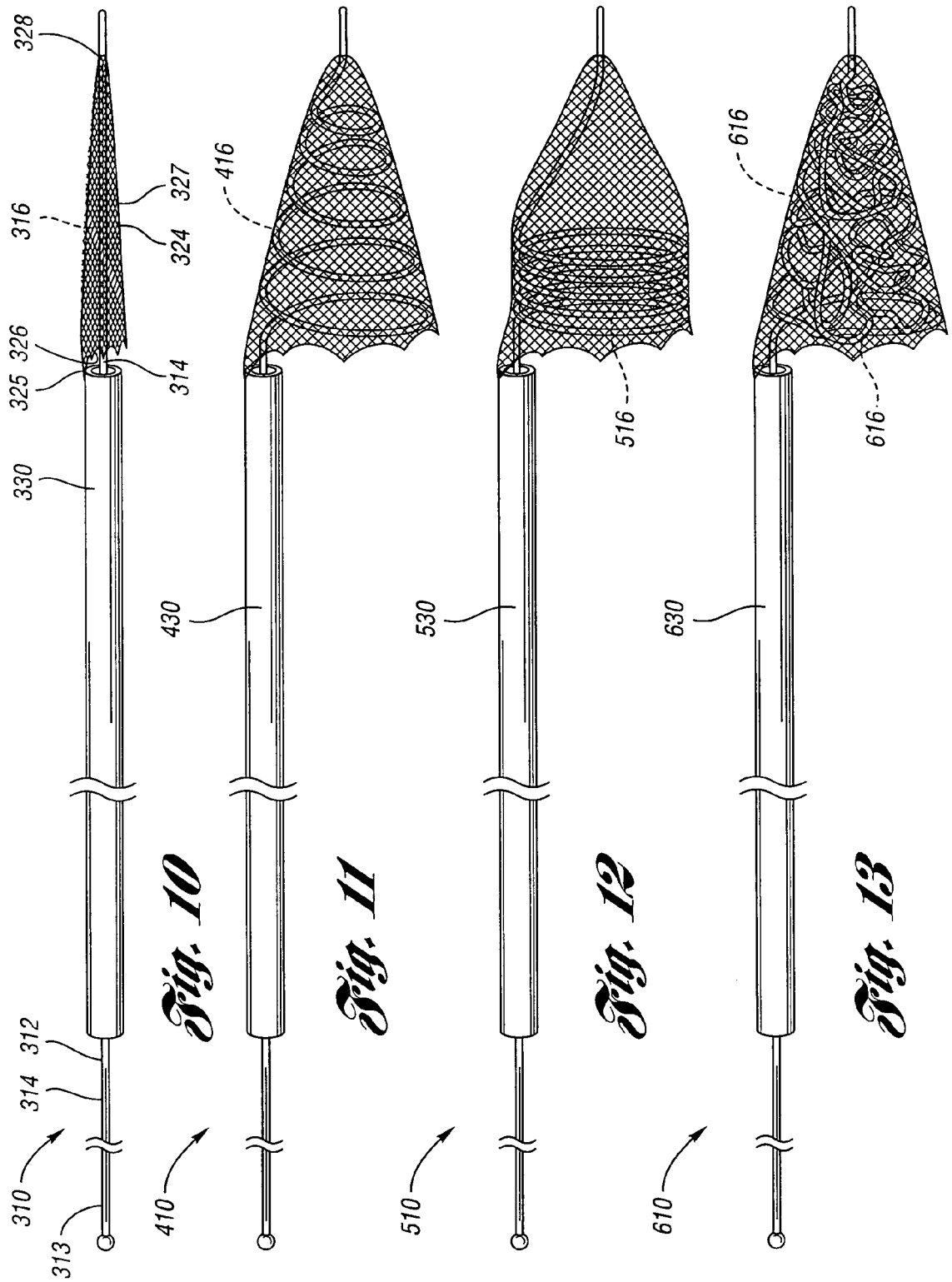

EMBOLIC PROTECTION DEVICE HAVING REDUCED PROFILE

CROSS-REFERENCE TO RELATED APPLICATION

This application claims the benefit of U.S. Provisional Application No. 60/732,851, filed on Nov. 2, 2005, entitled "EMBOLIC PROTECTION DEVICE HAVING REDUCED PROFILE," the entire contents of which are incorporated herein by reference.

BACKGROUND OF THE INVENTION

The present invention relates to medical devices. More particularly, the present invention relates to embolic protection devices and methods for capturing emboli within a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation process is called atherosclerosis.

Depending on the degree of stenosis and the patient's overall condition, carotid artery stenosis has been treated with surgery. The procedure (with its inherent risks) is called carotid endarterectomy, which removes the plaque from the arterial walls. Carotid endarterectomy has proven to benefit patients with arteries substantially narrowed, e.g., by about 70% or more. For people with less narrowed arteries, e.g., less than about 50%, an anti-clotting drug may be prescribed to reduce the risk of ischemic stroke. Examples of these drugs are anti-platelet agents and anticoagulants.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the of the stent are pressed firmly against the inner surface of the vessel wall.

During the stenosis procedure however, there is a risk of such blood clots and thrombi being undesirably released into the blood flow within the vasculature. Embolic protection to capture emboli within the vasculature is a growing concern in the medical industry. Currently, there are a number of approaches for embolic protection to prevent emboli from traveling within the vasculature, causing an undesirable embolism, e.g., pulmonary embolism. For example, vena cava filters are more commonly being used for trapping blood clots and emboli in the vena cava filter to prevent pulmonary embolism. Also, anti-platelet agents and anticoagulants may be used to breakdown blood clots. Moreover, snares and baskets (e.g., stone retrieval baskets) are more commonly used for retrieving urinary calculi. Additionally, occlusion coils are commonly used to occlude aneurysms and accumulate thrombi in a body vessel. Embolic or distal protection devices have been implemented to capture emboli from a stenotic lesion ungoing angioplasty.

During delivery or retrieval of an embolic protection device, it is desired that the cross over profile of the device is maintained as small as possible to minimize contact with the stenotic lesion. Contact with the stenotic lesion increases the risk of blood clots and thrombi being undesirably released into the blood flow within the vasculature. Moreover, during retrieval of the embolic protection device, there is also a risk of the trapped emboli escaping therefrom. This may occur during retrieval of the device and emboli trapped therein.

Thus, there is a need to provide embolic protection devices having a reduced cross-sectional profile and methods for distally protecting and capturing emboli with devices having reduced cross-sectional profile within a body lumen during a stenosis procedure.

BRIEF SUMMARY OF THE INVENTION

The present invention generally provides an embolic protection device for capturing emboli during treatment of a stenotic lesion in a body vessel. The present invention provides a device having a reduced cross-sectional profile when being delivered or retrieved in a body vessel.

In one embodiment, the present invention provides a device for capturing emboli during treatment at a stenotic lesion in a body vessel. The device comprises a base having an expanded state and a collapsed state. The base includes proximal and distal portions, wherein the distal portion has a support portion configured to deploy in the body vessel when the base is in the expanded state. The device further comprises a filter portion disposed on the distal portion of the base. The filter portion includes a lip extending to a filter body. The filter portion is configured to engage the support portion when deployed to define an opening of the filter portion for capturing emboli. The filter portion extends from the lip to a filter end. The device further comprises a collector tube through which the base is slideably disposed for delivery and retrieval of the device.

In another embodiment, the present invention provides an embolic protection assembly for capturing emboli during treatment of a stenotic lesion in a body vessel. The assembly comprises a balloon catheter having a tubular body portion and an expandable balloon attached to and in fluid communication with the tubular body portion for angioplasty at the stenotic lesion. The expandable balloon has distal and proximal portions. The assembly further comprises the device coaxially disposed within the balloon catheter during treatment of the stenotic lesion in the body vessel.

In another example, the present invention provides a method for embolic protection during treatment of a stenotic lesion in a body vessel. The method comprises percutaneously introducing the balloon catheter in a body vessel and disposing the device in its collapsed state coaxially within the balloon catheter. The method further comprises deploying the device in the expanded state downstream from the stenotic lesion to capture emboli during treatment of the stenotic lesion.

Further objects, features, and advantages of the present invention will become apparent from consideration of the following description and the appended claims when taken in connection with the accompanying drawings.

BRIEF DESCRIPTION OF THE DRAWINGS

FIG. 1a is a side view of a device for capturing emboli in accordance with one embodiment of the present invention;

FIG. 1b is a cross-sectional view of the device in FIG. 1a taken along line 1b-1b;

FIG. 2 is a side view of the device of FIG. 1a in a partially expanded state;

FIG. 3 is a side view of the device of FIG. 1a in a fully expanded state;

FIG. 4 is a side view of the device of FIG. 1a in the collapsed state with captured emboli therein;

FIG. 5 is an enlarged view of the device of FIG. 4 in circle 5;

FIG. 6a is a side view of an emboli capture assembly in accordance with one embodiment of the present invention;

FIG. 6b is an exploded view of the assembly in FIG. 6a;

FIG. 7 is a flow chart of one method for capturing emboli during treatment of a stenotic lesion in a body vessel in accordance with one example of the present invention;

FIG. 10 is a side view of a device for capturing emboli in a collapsed state in accordance with yet another embodiment of the present invention;

FIG. 11 is a side view of another device in an expanded state;

FIG. 12 is a side view of an embolic capture device in accordance with still another embodiment of the present invention; and FIG. 13 is a side view of yet another device for capturing emboli in accordance with another embodiment of the present invention.

DETAILED DESCRIPTION OF THE INVENTION

Figure 8B:
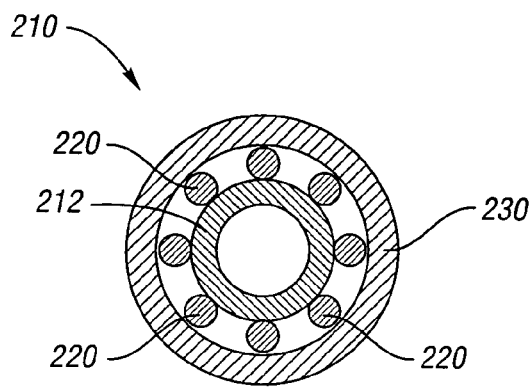
FIG. 8b is a cross-section view of the device in FIG. 8a taken along line 8b-8b.

The present invention generally provides an emboli protection device for capturing emboli during treatment of a stenotic lesion in a body vessel. Embodiments of the present invention provide a device having a reduced cross-sectional profile for delivery of the device during predilitation of the stenotic lesion, and a more simple and efficient way of delivering and retrieving the device. In one embodiment, the device includes a base having a support portion configured to deploy in the body vessel when the base is in an expanded state. A filter portion is configured to engage the support portion to minimize the cross-sectional profile of the device in the collapsed state and to open for capturing emboli in the expanded state. A collector which houses the base and the filter portion such that the device may function as a wire guide during delivery thereof in the body vessel.

FIG. 1a illustrates an embolic capture device 10 for capturing emboli in accordance with one embodiment of the present invention. As shown, the device in FIG. 1a is in a collapsed state and in FIGS. 2 and 3 is moveable to an expanded state. The device 10 comprises a base 12 having a proximal portion 13 and a distal portion 14. As shown, the distal portion 14 has a support portion 16 configured to deploy in the body vessel when the base 12 is in the expanded state.

In this embodiment, the support portion 16 includes a plurality of struts 20 extending from the distal portion 14 of the base 12 to engage the body vessel when in the expanded state. Of course, the support portion 16 may be comprised of other components such as a single strut or member to engage the body vessel in the expanded state. As shown in FIGS. 1b and 2, each strut 20 has a first end 22 attached to the distal portion 14 of the base and extends to a second end 23 or an anchor end 23 configured to engage the body vessel when deployed in the expanded state. In this embodiment, the support portion 16 is pre-formed to a predetermined shape upon deployment in the body vessel for enhanced engagement therewith. The base 12 may be made of any suitable material such as polymeric material, e.g., polypropylene, polyethylene, or polytetrafluoroethylene (PTFE).

The device further comprises a filter portion 24 attached proximally to the support portion 16 and distally to the base 12. As shown, the filter portion 24 includes a lip 26 distally extending to a filter body 27 and a closed filter end 28, and is configured to open when the device 10 is in the expanded state. This defines an opening 29 of the filter portion 24 for capturing emboli. In this embodiment, the lip 26 of the filter portion 24 is configured to attach or engage the support portion 16. Moreover, the filter end 28 is attached to the distal portion 14 of the base 12. Thus, the lip 26 opens when in the expanded state such that the opening 29 of the filter portion 24 faces the stenotic lesion upstream of the device 10.

In this embodiment, the lip 26 is attached to the second end 23 of each strut 20. The second end 23 of each strut 20 extends from the lip 26 to engage the body vessel when the support portion 16 is deployed in the expanded state. The extension of the second end 23 from the lip 26 allows for an enhanced anchoring mechanism on the body vessel during treatment of the stenotic lesion. As shown, the filter portion 24 is configured to expand and engage the body vessel when the support portion 16 is deployed.

In the collapsed state (see FIG. 1a), the support portion 16 and the filter portion 24 are arranged so that the cross-sectional profile of the device 10 is minimized. For example, the lip 26 is merely attached to the second end 23 of each strut 20 to allow the support portion 16 and the filter portion 24 to lie essentially in side-by-side or longitudinal relationship, thereby avoiding overlap when collapsed. Thus, the arrangement of the support portion 16 and the filter portion 24 in the collapsed state provides a reduced cross-sectional profile to the device.

As shown in FIGS. 3 and 4, the device further comprises a collector 30 through which the base 12 is slidably disposed for delivery and retrieval of the device. The collector 30 is preferably a tubular member for allowing components to be slidably disposed therethrough as mentioned below. As shown in FIGS. 4 and 5, the collector 30 includes a tubular body portion 32 through which the base 12 is slidably disposed and a detachable tubular tip portion 33 attached about the distal portion 14 of the base 12. In this embodiment, the tip portion 33 may be disengaged from the body portion 32 of the collector 30 by movably sliding the base 12 distally therefrom. Retracting the base 12 proximally engages the tip portion 33 with the body portion 32 of the collector 30. As mentioned, the base 12 is slidably moveable within the body portion 32 of the collector 30. The base 12 is configured to deploy the support portion 16 and the filter portion 24 from the distal end of the body portion 32 when moved distally relative thereto.

FIGS. 6a and 6b depict an embolic protection assembly 40 for capturing emboli during treatment of a stenotic lesion in a body vessel in accordance with another embodiment of the present invention. As shown, the assembly 40 comprises a balloon catheter 42 having a tubular body 44 and an expandable balloon 46 attached to and in fluid communication with the tubular body 44 for angioplasty at a stenotic lesion. In this embodiment, the assembly 40 comprises the embolic protection device mentioned above. The tubular body 44 is preferably made of soft flexible material such as silicon or any other suitable material. In this embodiment, the balloon catheter 42 may include an outer lumen and an inner lumen. The outer lumen may be in fluid communication with the balloon for inflating and deflating the balloon. The inner lumen is formed therethrough for percutaneous guidance through the body vessel.

As shown, the assembly 40 further includes an inner catheter 50 having a distal end 52 through which the balloon catheter 42 is disposed for deployment in the body vessel. The inner catheter 50 is preferably made of a soft, flexible material such as silicon or any other suitable material. Generally, the inner catheter 50 further has a proximal end and a plastic adaptor or hub to receive the embolic protection device and balloon catheter 42 to be advanced therethrough. The size of the inner catheter 50 is based on the size of the body vessel in which it percutaneously inserts, and the size of the balloon catheter 42.

As shown, the assembly 40 may also include a wire guide 60 configured to be percutaneously inserted within the vasculature to guide and the inner catheter 50 to a location adjacent a stenotic lesion. The wire guide 60 provides the inner catheter 50 (and balloon catheter 42) a path during insertion within the body vessel. The size of the wire guide 60 is based on the inside diameter of the inner catheter 50. However, it is to be understood that wire guide 60 is not necessary, since the device 10 may serve as a wire guide in the collapsed state.

In one embodiment, the balloon catheter 42 has a proximal fluid hub 62 in fluid communication with the balloon 46 via the outer lumen for fluid to be passed therethrough for inflation and deflation of the balloon 46 during treatment of the stenotic lesion.

In one example, the device 10 may be coaxially disposed through the inner lumen of the balloon catheter 42 prior to treatment of the stenotic lesion in the body vessel. The device 10 may then be guided through the inner lumen preferably from the hub and distally beyond the balloon 46 of the balloon catheter 42, exiting from the distal end of the inner or balloon catheter 42 to a location within the vasculature downstream of the stenotic lesion.

In this embodiment, the apparatus further includes a polytetrafluoroethylene (PTFE) introducer sheath 64 for percutaneously introducing the wire guide 60 and the inner catheter 50 in a body vessel. Of course, any other suitable material may be used without falling beyond the scope or spirit of the present invention. The introducer sheath 64 may have any suitable size, e.g., between about three-french to eight-french. The introducer serves to allow the inner catheter and balloon catheter to be percutaneously inserted to a desired location in the body vessel. The introducer sheath 64 receives the inner catheter 50 and provides stability to the inner catheter at a desired location of the body vessel. For example, the introducer sheath 64 is held stationary within a common visceral artery, and adds stability to the inner catheter 50, as the inner catheter is advanced through the introducer sheath 64 to a dilatation area in the vasculature.

When the distal end 52 of the inner catheter 50 is at a location downstream of the dilatation area in the body vessel, the balloon catheter 42 may be inserted therethrough to the dilatation area. The device may then be loaded at the proximal end of the balloon catheter 42 and advanced through the inner lumen thereof for deployment through its distal end.

FIG. 7 depicts a flow chart of one method 110 for embolic protection during treatment of stenotic lesion in a body vessel. The method 110 comprises percutaneously introducing the balloon catheter in a body vessel in box 112, after the inner catheter is disposed to a dilatation area within the body vessel. The physician may use any suitable means of verifying the placement of the balloon catheter at a dilatation area, e.g., fluoroscopy.

In this example, the method 110 further comprises disposing the embolic protection device in the collapsed state coaxially within the balloon catheter in box 114, once the balloon catheter is placed at the dilatation area. The method 110 further includes deploying the device in the expanded state downstream from the stenotic lesion to capture emboli during treatment of the stenotic lesion in box 116.

Figure 8A:
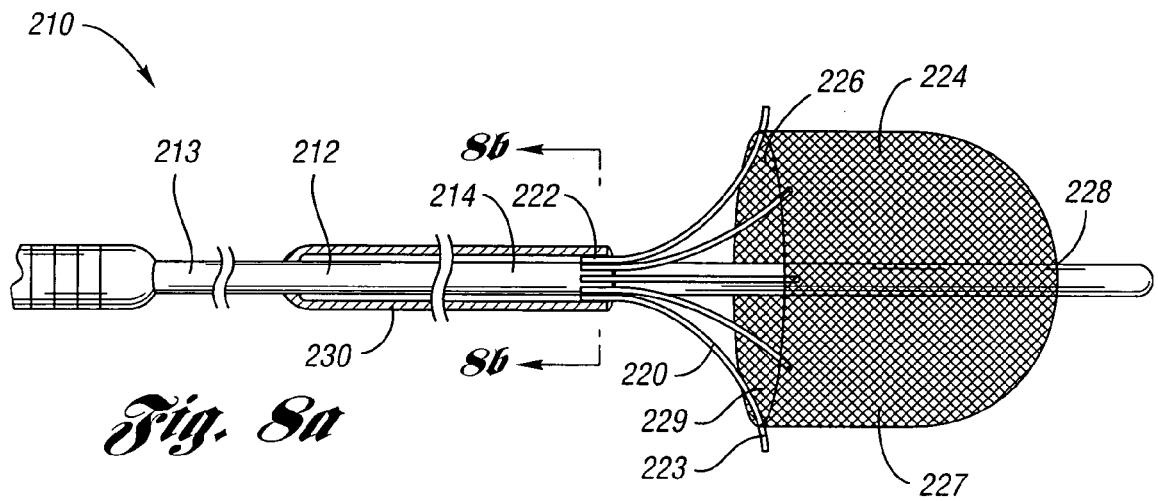
FIG. 8a is a side view of a device for capturing emboli in accordance with another embodiment of the present invention.
Figure 9:
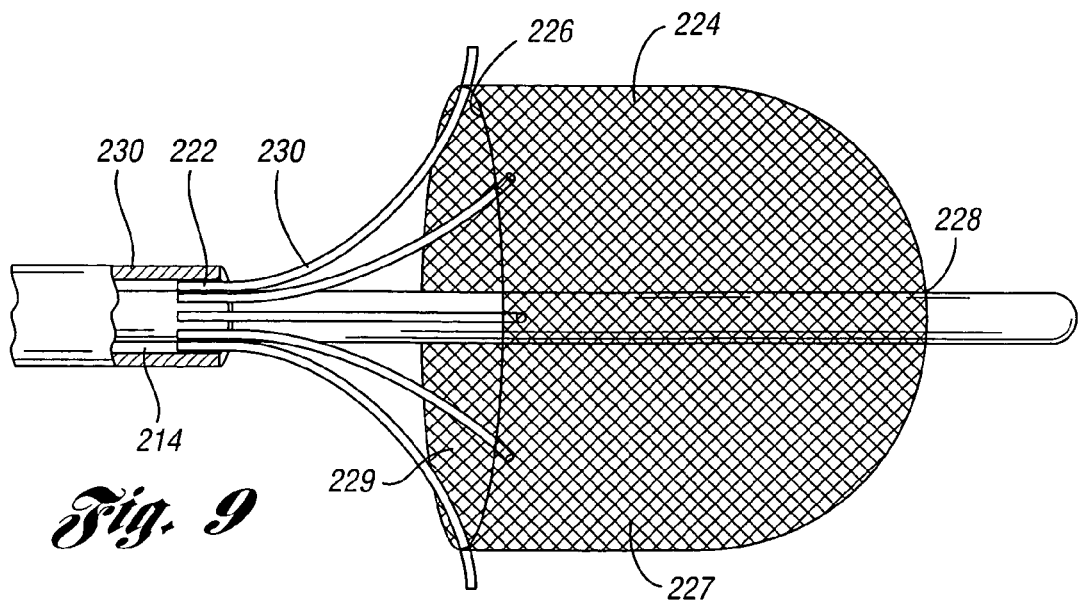
FIG. 9 is an enlarged view of the device in FIG. 8a in circle 9.

FIGS. 8a-9 illustrate a device 210 for capturing emboli during treatment of a stenotic lesion in a body vessel in accordance with another embodiment of the present invention. As with the device 10 mentioned above, this device 210 may be configured in expanded and collapsed states. As shown, the device comprises a base 212 having proximal and distal portions 213 and 214. The distal portion 214 of the base 212 has a support portion 216 configured to deploy in the body vessel in the expanded state. Preferably, base 212 is a tubular member, allowing a wire guide, e.g., wire guide 60 mentioned above, to be slidably inserted therethrough for percutaneous guidance within the body vessel.

As shown in FIGS. 8a and 8b, the support portion 216 includes a plurality of struts 220 attached about the base 212 and extends radially outwardly from the distal portion 214 of the base 212 to engage the body vessel when disposed therein and in the expanded state. Each of the struts 220 has a first end 222 attached about the base 212 and extends to a second or anchor end 223 configured to engage the body vessel when deployed. Preferably, the support portion 216 is pre-formed to a predetermined shape so that upon deployment the struts extend radially outwardly to engage the body vessel. The support portion 216 may be attached about the base 212 by any suitable means including thermal bonding, sonic boding, and adhesive bonding.

As shown in FIGS. 8a and 9, the device 210 further comprises a filter portion 224 disposed about the distal portion 214 of the base 212 and on each of the struts 220. In this embodiment, the filter portion 224 is configured to engage and attach to the support portion 216. The filter portion 224 comprises a lip 226 that is attached to the struts 220. The anchor end 223 of each strut 220 extends from the lip 226 to engage the body vessel when the support portion 216 is deployed. When the device 210 is deployed in a body vessel, the struts 220 and the lip 226 of the filter portion 224 expand, defining an opening 229 of the filter portion for capturing emboli.

In this embodiment, the lip 226 extends to a filter body 227 which ends at a closed filter end 228. Preferably, the closed filter end 228 is attached to the distal portion 214 of the base 212 as shown. This may be accomplished by any suitable manner, e.g., by thermal, sonic, or adhesive bonding techniques. In use, the filter portion 224 expands when the support portion 216 is deployed and in the expanded state. The filter portion 224 is configured to expand and engage the body vessel when the support portion 216 is deployed for capturing emboli in a body vessel.

As shown in FIGS. 8a and 9, the device 210 further comprises a collector 230 through which the base 212 is slidably disposed for delivery and retrieval of the device 210. The collector 230 is preferably a tubular member, e.g., a catheter, for allowing components to be slidably disposed therethrough as mentioned below. As shown, the collector 230 includes a tubular body portion 231 through which the base 212 is slidably disposed. As mentioned, the base 212 is slidably moveable within the body portion 231 of the collector 230. The base 212 is configured to deploy the support portion 216 and the filter portion 224 from the distal end of the body portion 231 when moved distally relative thereto. Thus, the support portion 216 expands when deployed from the collector 230 and is configured to collapse as the collector 230 is distally moved over the struts 220.

FIG. 10 illustrates another device 310 for capturing emboli during treatment of a stenotic lesion in a body vessel in accordance with another embodiment of the present invention. The device 310, shown in the collapsed state, comprises a base 312 having expanded and collapsed states, and having proximal and distal portions 313 and 314. The distal portion 314 includes a support portion 316 configured to deploy in the body vessel in the expanded state. In this embodiment, the support portion 316 is pre-formed to a predetermined shape upon deployment in the expanded state. This may be accomplished by any suitable manner, e.g., shape memory materials may be employed as mentioned below.

The device further comprises a filter portion 324 attached to the distal portion 314 of the base 312 and to a collector 330. The filter portion 324 includes a lip 326 that attaches to the collector 330 at a point 334, thereby minimizing the cross-sectional profile of the device in the collapsed state. The lip 326 defines an opening 329 of the filter portion 324 for capturing emboli and extends to a filter body 327 which ends at a filter end 328. In the expanded state, the support portion 316 expands to its predetermined state and engages the filter portion 324. Thus, the filter portion 324 receives the support portion 316 in the expanded state for capturing emboli when deployed in a body vessel.

The device 310 further comprises a collector 330 through which the base 312 is slideably disposed for delivery and retrieval of the device 310. In this embodiment, the collector 330 is a tubular member allowing the base 312 to be slidably movable relative thereto. The support portion 316 is expanded when deployed from the collector 330 and is configured to collapse as the support portion 316 is retracted or as the collector tube distally rides over the base.

FIGS. 11-13 depict different embodiments of the device having various pre-formed or predetermined shapes in the expanded state. FIG. 11 depicts a device 410 comprising a support portion 416 having a tapered spiral shape in the expanded state. FIG. 12 illustrates a device 510 comprising a support portion 516 having a spiral or helical configuration in the expanded state. Furthermore, FIG. 13 depicts a device 610 comprising a support portion 616 having a random serpentine configuration in the expanded state.

The filter portion of the devices mentioned above may be comprised of any suitable material to be used for capturing emboli from the stenotic lesion during treatment thereof. In one embodiment, the filter portion is made of connective tissue material for capturing emboli. In this embodiment, the connective tissue comprises extracellular matrix (ECM). As known, ECM is a complex structural entity surrounding and supporting cells that are found within mammalian tissues. More specifically, ECM comprises structural proteins (e.g., collagen and elastin), specialized protein (e.g., fibrillin, fibronectin, and laminin), and proteoglycans, a protein core to which are attached are long chains of repeating disaccharide units termed of glycosaminoglycans.

Most preferably, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In this embodiment, SIS is used to temporarily adhere the filter portion to the walls of a body vessel in which the device 10 is deployed. SIS has a natural adherence or wettability to body fluids and connective cells comprising the connective tissue of a body vessel wall. Due to the temporary nature of the duration in which the device 10 is deployed in the body vessel, host cells of the wall will adhere to the filter portion but not differentiate, allowing for retrieval of the device 10 from the body vessel.

In other embodiments, the filter portion may also be made of a mesh/net cloth, nylon, polymeric material, Teflon, or woven mixtures thereof without falling beyond the scope or spirit of the present invention.

The support portion of any of the devices mentioned above may be comprised of any suitable material such as a super-elastic material (e.g. Nitinol), stainless steel wire, cobalt-chromium-nickel-molybdenum-iron alloy, or cobalt-chrome alloy. It is understood that the support portion may be formed of any other suitable material that will result in a self-opening or self-expanding support portion, such as shape memory alloys. Shape memory alloys have a property of becoming rigid, that is, returning to a remembered state, when heated above a transition temperature. A shape memory alloy suitable for the present invention may comprise Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one alternate embodiment, the support portion may be made from Nitinol with a transition temperature that is slightly below normal body temperature of humans, which is about 98.6° F. Although not necessarily a preferred embodiment, when the support portion is deployed in a body vessel and exposed to normal body temperature, the alloy of the support portion will transform to austenite, that is, the remembered state, which for one embodiment of the present invention is the expanded configuration when the support portion is deployed in the body vessel. To collapse the support portion, the support portion is cooled to transform the material to martensite which is more ductile than austenite, making the support portion more malleable. As such, the support portion can be more easily collapsed and pulled into a lumen of a catheter for removal.

In another alternate embodiment, the support portion may be made from Nitinol with a transition temperature that is above normal body temperature of humans, which is about 98.6° F. Although not necessarily a preferred embodiment, when the support portion is deployed in a body vessel and exposed to normal body temperature, the support portion is in the martensitic state so that the support portion is sufficiently ductile to bend or form into a desired shape, which for the present invention is an expanded configuration. To remove the support portion, the support portion is heated to transform the alloy to austenite so that the support portion becomes rigid and returns to a remembered state, which for the support portion in a collapsed configuration.

While the present invention has been described in terms of preferred embodiments, it will be understood, of course, that the invention is not limited thereto since modifications may be made to those skilled in the art, particularly in light of the foregoing teachings.

The invention claimed is:

1. A device for capturing emboli during treatment of a stenotic lesion in a body vessel, the device comprising:
   a base including proximal and distal portions, the distal portion having a support portion having an expanded state and a collapsed state, the support portion configured to deploy in the body vessel when in the expanded state, the support portion including a plurality of struts extending from the distal portion of the base, each strut having a first end attached to the distal portion of the base and a second anchor end configured to engage the body vessel, each strut extending distally from the first end to the second anchor end;
   a filter portion disposed on the distal portion of the base, the filter portion including a lip distally attached to the struts and extending to a filter body, the filter portion being configured to engage the support portion when deployed to define an opening of the filter portion for capturing emboli, the struts extending distally and radially outwardly past the lip to the second anchor ends to engage the body vessel when the support portion is in the expanded state, the struts extending distally but not radially outwardly past the lip to the second anchor ends when the support portion is in the collapsed state, the filter portion extending from the lip to a filter end; and
   a collector comprising a tubular body portion through which the base is slideably disposed for delivery and retrieval of the device, the tubular body portion having a proximal end and a distal end, wherein the base is configured to deploy the support portion from the distal end of the tubular body portion when the base is moved distally relative to the tubular body portion, and wherein the support portion is configured to self-expand into the expanded state when the support portion is deployed from the distal end of the tubular body portion;
   wherein the distal portion of the base extends distally within the support portion and the filter portion through the filter end, the filter end being attached to the distal portion of the base, the distal portion of the base including an enclosed portion enclosed by the support portion and the filter portion between the first ends of the struts and the filter end, the enclosed portion of the base not including a radially expandable balloon.

2. The device of claim 1 wherein the base is a tubular member.

3. The device of claim 2 further comprising a wire guide slideably disposed through the base and the filter portion for percutaneous guidance.

4. The device of claim 1 wherein the support portion is configured to collapse as the tubular body portion is distally moved over the struts.

5. The device of claim 1 wherein the support portion is pre-formed to a predetermined shape upon deployment from the tubular body portion.

6. The device of claim 1 wherein the filter body is configured to expand and engage the body vessel when the support portion is deployed.

7. The device of claim 1 wherein the collector further comprises a detachable tip portion, the base being connected to the tip portion.

8. The device of claim 1 wherein the lip of the filter portion is attached to the support portion to define the opening of the filter portion for capturing emboli when the support portion is deployed.

9. An embolic protection assembly for capturing emboli during treatment of a stenotic lesion in a body vessel, the assembly comprising:
   a balloon catheter having a tubular body portion and an expandable balloon attached to and in fluid communication with the tubular body portion for angioplasty at the stenotic lesion, the expandable balloon having distal and proximal portions; and
   a device for capturing emboli coaxially disposed within the balloon catheter during treatment of the stenotic lesion in the body vessel, the device comprising:
      a base including proximal and distal portions, the distal portion having a support portion having an expanded state and a collapsed state, the support portion configured to deploy in the body vessel when in the expanded state, the support portion including a plurality of struts extending from the distal portion of the base, each strut having a first end attached to the distal portion of the base and a second anchor end, each strut extending distally from the first end to the second anchor end;
      a filter portion disposed on the distal portion of the base, the filter portion including a lip distally attached to the struts and extending to a filter body, the filter portion being configured to engage the support portion when deployed to define an opening of the filter portion for capturing emboli, the filter portion extending from the lip to a filter end, wherein each strut extends from the lip to the second anchor end, the struts being configured to extend distally and radially outwardly past the lip to the second anchor ends to engage the body vessel when the support portion is in the expanded state, the struts being configured to extend distally but not radially outwardly past the lip to the second anchor ends when the support portion is in the collapsed state; and
      a collector tube through which the base is slideably disposed for delivery and retrieval of the device, the collector tube having a proximal end and a distal end, wherein the base is configured to deploy the support portion from the distal end of the collector tube when the base is moved distally relative to the collector tube, and wherein the support portion is configured to self-expand into the expanded state when the support portion is deployed from the distal end of the collector tube;
   wherein the distal portion of the base extends distally within the support portion and the filter portion through the filter end, the filter end being attached to the distal portion of the base, the distal portion of the base including an enclosed portion enclosed by the support portion and the filter portion between the first ends of the struts and the filter end, the enclosed portion of the base not including a radially expandable balloon.

10. The assembly of claim 9 wherein the support portion is configured to collapse as the collector tube is distally moved over the struts.

* * * * *